US008815300B2

(12) United States Patent
Comanor

(10) Patent No.: US 8,815,300 B2
(45) Date of Patent: Aug. 26, 2014

(54) COMPOSITION AND METHODS FOR RELIEF OF NEUROPATHOLOGICAL PAIN

(75) Inventor: Jeffrey Comanor, Kennesaw, GA (US)

(73) Assignee: Coastal Biologic Solutions, Marietta, GA (US)

( * ) Notice: Subject to any disclaimer, the term of this patent is extended or adjusted under 35 U.S.C. 154(b) by 0 days.

(21) Appl. No.: 13/060,517

(22) PCT Filed: Aug. 28, 2009

(86) PCT No.: PCT/US2009/055281
§ 371 (c)(1),
(2), (4) Date: May 3, 2011

(87) PCT Pub. No.: WO2010/025316
PCT Pub. Date: Mar. 4, 2010

(65) Prior Publication Data
US 2011/0262418 A1    Oct. 27, 2011

Related U.S. Application Data

(60) Provisional application No. 61/092,892, filed on Aug. 29, 2008.

(51) Int. Cl.
*A61K 33/42*  (2006.01)
*A61K 31/122* (2006.01)
*A61P 29/00*  (2006.01)
*A61K 31/40*  (2006.01)

(52) U.S. Cl.
CPC ..................... *A61K 31/40* (2013.01)
USPC ........................... 424/605; 514/690

(58) Field of Classification Search
USPC ....................................................... 424/94.1
See application file for complete search history.

(56) References Cited

U.S. PATENT DOCUMENTS

| | | | |
|---|---|---|---|
| 6,352,712 B1 * | 3/2002 | Lukaczer et al. | 424/439 |
| 7,258,880 B2 | 8/2007 | Piva et al. | |
| 2005/0009796 A1 | 1/2005 | Goodchild et al. | |
| 2005/0227961 A1 * | 10/2005 | Kucharik et al. | 514/211.13 |
| 2006/0094685 A1 * | 5/2006 | Endo et al. | 514/49 |
| 2007/0149466 A1 | 6/2007 | Milburn et al. | |

FOREIGN PATENT DOCUMENTS

EP            1323422    * 12/2002   ......... A61K 31/5517

OTHER PUBLICATIONS

Stedman's Online. 2012.*
Sahley BJ. Alpha KG—fatigue fighter. Pain & Stress Publications. 2006.*
Nihalani et al. Fibromyalgia—a review for the psychiatrist. Psychiatry. 2006;44-60.*
Magnesium. IBISmedical. 2000.*
FMS Information Resource Guide. Will vitamins and supplements help treat fibromyalgia syndrome? Immune Support. 2000.*
Chemical characteristics. The Olive Oil Source. 2012.*
Byrnes S. Solving the puzzle of fibromyalgia. 2004. 1-6.*
Stavarache et al. Fatty acids methyl esters from vegetable oil by means of ultrasonic energy. Ultrasonics Sonochemistry. 2005;12:367-372.*
Santos et al. Thermoanalytical, kinetic and theological parameters of commercial edible vegetable oils. Journal of Thermal Analysis and Calorimetry. 2004;75:419-428.*
Choline. WebMD. 2009.*
Dr. Hoffman's NT Factor Energy, http://www.drhoffman.com/downloads/ntfactorenergy.pdf, Wayback Machine dates to Oct. 2007.*
Dr. Murphree's, http://www.drmurphreestore.com/healthnews504.html, dated Sep. 2007.*
ABC Homeopathy, http://abchomeopathy.com/r.php/Ph-ac, accessed Oct. 3, 2013, wayback machine archived page dated Oct. 8, 2003.*
HolisticOnline; http://www.holistic-online.com/remedies/cfs/cfs__homeopathy.htm, Feb. 19, 2001.*
Dr. Teitelbaum's treatment protocol; http://www.immunesupport.com/chronic-fatigue-syndrome-teitelbaum.htm, Nov. 27, 2006.*
The International Search Report and Written Opinion dated Nov. 3, 2009.
Carrero, et al., "Daily Supplementation with (n-3) PUFAs, Oleic Acid, Folic Acid, and Vitamins B-6 and E Increases Pain-Free Walking Distance and Improves Risk Factors in Men with Peripheral Vascular Disease," J. Nutr. Jun. 2005, vol. 135:1393-1399.

* cited by examiner

*Primary Examiner* — Mina Haghighatian
*Assistant Examiner* — Erin Hirt
(74) *Attorney, Agent, or Firm* — Thomas Horstemeyer, LLP

(57) ABSTRACT

The formulations of the present disclosure alter the perception of pain, especially as experienced by subjects reporting the characteristic features associated with the syndrome known as fibromyalgia. The present disclosure encompasses formulations for the relief of symptoms associated with neuropathy pain, where the formulations comprise orthophosphoric acid, a vegetable oil comprising an esterified mono-unsaturated fatty acid, and folic acid. The formulations can further comprise magnesium citrate, magnesium aspartate, malic acid, L-carnitine, alpha-ketoglutaric acid, co-enzyme Q10, glycerol, inositol, and cholinebitartrate, optionally Q10, and riboflavin to provide a yellow color to the formulation. Another aspect of the disclosure are methods for alleviating neuropathy related pain in subject animal or human, comprising: providing to a subject an effective dose of a formulation comprising orthophosphoric acid, a mono-unsaturated fat, folic acid, and water.

6 Claims, No Drawings

COMPOSITION AND METHODS FOR RELIEF OF NEUROPATHOLOGICAL PAIN

CROSS-REFERENCE TO RELATED APPLICATION

This application claims priority to PCT Application No. US/2009/055281, filed Aug. 28, 2009 and entitled "COMPOSITION AND METHODS FOR RELIEF OF NEUROPATHOLOGICAL PAIN", and which also claims priority to U.S. Provisional Application No. 61/092,892, entitled "COMPOSITION AND METHODS FOR RELIEF OF NEUROPATHOLOGICAL PAIN" filed on Aug. 29, 2008, the entirety of which is herein incorporated by reference in its entirety.

TECHNICAL FIELD

The present disclosure is generally related to a composition and methods for the relief of symptoms associated with neuropathy pain. The present disclosure is especially related to compositions and methods for the relief of pain associated with fibromyalgia

BACKGROUND

Fibromyalgia is a chronic disorder characterized by widespread musculoskeletal pain and tenderness to palpation at specific tender points. In addition, fibromyalgia patients often describe other symptoms such as fatigue, sleep disturbances, headache or cognitive dysfunction associated with the syndrome. The American College of Rheumatology has defined fibromyalgia as pain in all four quadrants combined with axial skeletal pain, and at least 11 of 18 tender point sites. Widespread pain must have been present for at least 3 months. Tender points, the diagnostic hallmark of fibromyalgia, are examples of hyperalgesia, thought to be due to central sensitization. Patients with fibromyalgia have quantitatively altered perception compared to pain-free patients, suggesting that people with fibromyalgia process sensory information differently, most likely due to changes in the central processing of pain at the spinal level.

Patients often report widespread pain over all parts of the body which often seems to arise in the muscles. The pain shows varying intensities that wax and wane over time, it is profound, widespread and chronic, and is often severely debilitating, having profound effects on the quality of life of the patients.

Typically, the pain is described as deep muscular aching, throbbing, twitching, stabbing and shooting pain. Neurological complaints such as numbness, tingling and burning are often present. The severity of the pain and stiffness is often worse in the morning. Aggravating factors that affect pain include cold/humid weather, non-restorative sleep, physical and mental fatigue, excessive physical activity, physical inactivity, anxiety and stress. Additionally to pain, patients commonly complain of fatigue in form of an all-encompassing exhaustion that interferes with even the simplest daily activities. Within the spectrum of symptoms are a decreased sense of energy, disturbances of sleep, problems with memory and concentration and varying degrees of anxiety and depression.

Certain other medical conditions are sometimes associated with fibromyalgia, such as tension headaches, migraine, irritable bowel syndrome, overactive bladder, pelvic pain, premenstrual tension syndrome, cold intolerance, dry eyes and mouth, anxiety, depression, ringing in the ears, dizziness, vision problems and others. Patients with established rheumatoid arthritis, lupus (SLE) and Sjogren's syndrome often develop fibromyalgia symptoms during the course of their disease.

The complexity of the syndrome, with multiple and highly diverse symptoms described by the patients has meant that effective and long-term relief, above all of the pain, has proved elusive. Common analgesics have limited effectiveness, especially over the long-term.

SUMMARY

The formulations of the present disclosure alter the perception of pain, especially as experienced by subjects reporting the characteristic features associated with the syndrome known as fibromyalgia. The formulations of the present disclosure further provide relief from pain symptoms associated with inflammatory conditions such as rheumatoid arthritis, lupus and the like. One aspect of the present disclosure encompasses formulations for the relief of symptoms associated with neuropathy pain, where the formulations comprise orthophosphoric acid, a vegetable oil comprising an esterified mono-unsaturated fatty acid, and folic acid.

The formulations can further comprise an aqueous carrier, wherein the aqueous carrier optionally comprises a vitamin, a nutraceutical, a coloring agent, a flavoring agent, or a combination thereof.

In some embodiments, the vegetable oil can be olive oil.

Embodiments of the formulation can further comprise at least one of the group consisting of: magnesium citrate, magnesium aspartate, malic acid, L-carnitine, alpha-ketoglutaric acid, co-enzyme Q10, glycerol, inositol, and choline bitartrate.

Some embodiments of the disclosure can comprise magnesium citrate, magnesium aspartate, malic acid, L-carnitine, alpha-ketoglutaric acid, co-enzyme Q10, glycerol, inositol, and choline bitartrate.

One embodiment of the formulation comprises, in a final volume of 100 ml: ortho-phosphoric acid, about 8.5 ml; vegetable oil, about 1.2 ml; folic acid, about 2.1 mg; malic acid, about 85 mg; magnesium citrate, about 170 mg; magnesium aspartate, about 17 mg; L-carnitine, about 85 mg; alpha-ketoglutaric acid, 127 mg; choline bitartrate, about 11 mg; inositol, about 23 mg; glycerol between about 0.1 ml and about 0.5 ml; and water. This embodiment of the disclosure can further comprise Q10 between about 0.05 mg and about 1000 mg, and riboflavin, wherein the amount of riboflavin provides a yellow color to the formulation.

Another aspect of the disclosure encompasses methods for alleviating neuropathy related pain in subject animal or human, comprising: providing to a subject in need of relief from neuropathy related pain an effective dose of a formulation comprising orthophosphoric acid, a mono-unsaturated fat, folic acid, and water, wherein the amount of orthophosphoric acid is between about 4 ml to about 80 ml, the amount of mono-unsaturated fatty acid is between about 0.25 ml to about 20 ml, the amount of folic acid is between about 1 mg and 2000 mg, and the amount of water is about 200 mls.

In the embodiments of the methods of this aspect of the disclosure, the formulation can be provided to the subject sublingually.

In the embodiments of the methods of this aspect of the disclosure, the formulation can be diluted with water and the subject receives the formulation orally.

DETAILED DESCRIPTION

Before the present disclosure is described in greater detail, it is to be understood that this disclosure is not limited to particular embodiments described, and as such may, of course, vary. It is also to be understood that the terminology used herein is for the purpose of describing particular embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the disclosure. The upper and lower limits of these smaller ranges may independently be included in the smaller ranges and are also encompassed within the disclosure, subject to any specifically excluded limit in the stated range. Where the stated range includes one or both of the limits, ranges excluding either or both of those included limits are also included in the disclosure.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of medicine, organic chemistry, biochemistry, molecular biology, pharmacology, and the like, which are within the skill of the art. Such techniques are explained fully in the literature.

It must be noted that, as used in the specification and the appended claims, the singular forms "a," "an," and "the" include plural referents unless the context clearly dictates otherwise.

As used herein, the following terms have the meanings ascribed to them unless specified otherwise. In this disclosure, "comprises," "comprising," "containing" and "having" and the like can have the meaning ascribed to them in U.S. Patent law and can mean "includes," "including," and the like; "consisting essentially of" or "consists essentially" or the like, when applied to methods and compositions encompassed by the present disclosure refers to compositions like those disclosed herein, but which may contain additional structural groups, composition components or method steps (or analogs or derivatives thereof as discussed above). Such additional structural groups, composition components or method steps, etc., however, do not materially affect the basic and novel characteristic(s) of the compositions or methods, compared to those of the corresponding compositions or methods disclosed herein. "Consisting essentially of" or "consists essentially" or the like, when applied to methods and compositions encompassed by the present disclosure have the meaning ascribed in U.S. Patent law and the term is open-ended, allowing for the presence of more than that which is recited so long as basic or novel characteristics of that which is recited is not changed by the presence of more than that which is recited, but excludes prior art embodiments.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±6%, ±7%, ±8%, ±9%, or ±10%, or more of the numerical value(s) being modified.

DEFINITIONS

In describing and claiming the disclosed subject matter, the following terminology will be used in accordance with the definitions set forth below.

The term "formulation" as used herein refers to a composition that may be a stock solution of the components, or a composition, preferably including a dilutant such as water or other pharmaceutically acceptable carrier, that may be available for distribution including to a patient or physician.

The term "vegetable oil" as used herein refers to oils comprising a triglyceride ester of a mono-unsaturated long-chain fatty. Vegetable oils for use in the formulations of the disclosure include, but are not limited to, coconut oil, corn oil, cottonseed oil, olive oil, palm oil, peanut oil rapeseed oil, safflower oil, sesame oil, soybean oil, and sunflower oil. For example, but not intending to be limiting, olive oil is composed mainly of the mixed triglyceride esters of oleic acid and palmitic acid and of other fatty acids, along with traces of squalene (up to 0.7%) and sterols (about 0.2% phytosterol and tocosterols). The composition varies by cultivar, region, altitude, time of harvest, and extraction process. Olive oil further comprises natural products with potent antioxidant properties which give extra-virgin unprocessed olive oil its bitter and pungent taste and which are esters of tyrosol, hydroxytyrosol, oleocanthal and oleuropein.

The term "mono-unsaturated fat" as used herein refers to fatty acids that have a single double bond in the fatty acid chain and all of the remainder of the carbon atoms in the chain are single-bonded. By contrast, polyunsaturated fatty acids have more than one double bond.

Fatty acids are long-chained molecules having a methyl group at one end and a carboxylic acid group at the other end. Fatty acid fluidity increases with increasing number of double bonds. Therefore, mono-unsaturated fatty acids have a higher melting temperature than polyunsaturated fatty acids but lower than saturated fatty acids. Mono-unsaturated fatty acids are liquids at room temperature and semisolid or solid when refrigerated. Common mono-unsaturated fatty acids are palmitoleic acid, cis-vaccenic acid, and oleic acid. Palmitoleic acid has 16 carbon atoms with the first double bond occurring 7 carbon atoms away from the methyl group (and 9 carbons from the carboxyl end). It can be lengthened to the 18-carbon cis-vaccenic acid. Oleic acid has 18 carbon atoms with the first double bond occurring 9 carbon atoms away from the methyl group. I The term "coloring agent" as used herein refers to any agent pharmaceutically acceptable or otherwise certified as same for human ingestion, such as, but not limited to, riboflavin, and which may impart to the formulations of the disclosure either an attractive appearance or to distinguish the formulation from a colorless liquid such as water, or to provide a means to determine the dilution of a formulation.

The term "flavoring agent" as used herein refers to any agent pharmaceutically acceptable or otherwise certified as same for human ingestion that imparts to a formulation of the disclosure a flavor that may increase the palatability of the composition to a patient receiving the formulation.

The term "neuropathy" as used herein refers to any diseases of the nervous system. Peripheral neuropathy refers to pain associated with muscle weakness, impaired reflexes and the like such as, but not limited to, polyneuropathy.

The term "fibromyalgia' as used herein refers to chronic and frequently difficult-to-manage pain in muscle and soft tissues surrounding the joints. Associated with pain are other symptoms that may not be present in the entirety such as depression, memory loss, anxiety and sleeplessness.

DESCRIPTION OF THE DISCLOSURE

The embodiments of the present disclosure encompass formulations and methods of use thereof intended for the effective relief of peripheral neuropathological, neuromuscular pain, and other symptoms typically associated with the syndrome known as fibromyalgia. The formulations and methods of the disclosure are further intended to provide relief to symptoms other than pain that may be associated with fibromyalgia, including but not limited to, depression, memory loss, anxiety and sleeplessness. The formulations of the disclosure may also be beneficial in the relief of pain or ancillary symptoms associated with inflammatory diseases, including, but not limited to, rheumatoid arthritis, lupus, polyneuropathic disease and the like. It has been shown, that the combination of orthophosphoric acid, a mono-unsaturated fatty acid (in particular the naturally derived preparation of such fatty acids in olive oil), and folic acid, provide rapid relief from the palpation-triggered pain symptoms of fibromyalgia. Pain relief and alleviation of mood-altering conditions such as depression, anxiety and the like have also been reported when the formulations of the disclosure are administered to subjects apparently experiencing inflammatory syndromes including lupus, rheumatoid arthritis and chronic allergies.

The formulations of the disclosure have been administered to a group of patients, both male and female and of ages ranging from about 19 to about 75 years. Controlled studies, where some patients were administered placebo control formulations such as water dispensed to the patients in a manner identical to that of the actual formulations, showed that the placebos had no reported effect in alleviating the symptoms of fibromyalgia. Additionally, no adverse side effects were reported. Many patients also reported that with the formulations of the disclosure, not only was there immediate or rapid relief of the pain symptoms that had afflicted many for years, but other symptoms associated with the fibromyalgia syndrome, such as depression were lessened or relieved. Many of the treated subjects experience long-lasting, if not permanent, relief from fibromyalgia debilitation.

The formulation of the present disclosure appears, therefore, to alter the perception of pain, especially as experienced by subjects reporting the characteristic features associated with the syndrome known as fibromyalgia. While not wishing to be held to any one theory, it is believed that the pain symptoms reported by subjects repeatedly suffering from the malady are due to perceptions generated within the brain, rather than generated at the perceived pain points. It is, therefore, possible that the action of the formulations of the present disclosure may alter the set point, and diminish the intensity, of neural firing, thereby raising the critical point at which pain is perceived. The overall effect is to normalize the sensations at the tender points palpated.

The present disclosure, therefore, provides formulations ranging from an undiluted composition to formulations more suitable for administration to patients, including by low dose deposition directly to oral tissue, or in a more diluted fashion intended to be ingested orally by the patient.

The administered dose is dependent on the severity of the perceived pain of the subject. An initial dose of between about 9 ml and about 12 ml of the stock solution, as shown in Example 4, is diluted in between about 1.5 fluid ounces and 3.0 fluid ounces of water. The subject receives the full diluted dose and is retested for pain severity within about 30 secs. If there is no evident relief of pain experienced, a second dose of the formulation may be given. The second dose is between about 6 ml and about 9 ml of the stock solution diluted by the same amount of water as before, and again fully ingested by the subject. The subject is repalpated after about 30 secs. On rare occasions, pain symptoms still show no sign of diminishing, and a third dose may be required. The full effects of symptom relief may be seen within 15 minutes of administering the first dose.

In the early stage of the treatment, most subjects appear to require about 3 ml to about 4 ml of the formulation presented in Example 4. The exact amount administered to the patient depends, however, on the severity of the symptoms—the greater the discomfort, the more of the formulation is administered. After about 1 to 2 weeks of treatment, the dose can typically be reduced to about 3 mls of the formulation diluted in water, and taken by the subject every 7 to 8 hours. If the symptom relief is sufficiently controlled after more than a month, the dosage may be reduced even further to between about 0.5 to about 3 mls every 8 to 10 hours. Typically, subjects, after about 6 months of taking the formulation may cease further treatment for several weeks or months. In many cases, full and apparently permanent relief of pain has been described by the subjects.

As an alternative to the ingestion of the diluted formulation by the subject, the undiluted formulation may be administered undiluted sublingually, i.e under the tongue. It has been observed that this method provides pain relief to areas of fibromyalgia subjects above the waist-line within about 3-5 secs. Sublingual administration of the formulation rarely, however, results in complete relief in all regions of the body.

One aspect of the present disclosure encompasses formulations for the relief of symptoms associated with neuropathy pain, where the formulations comprise orthophosphoric acid, a vegetable oil comprising an esterified mono-unsaturated fatty acid, and folic acid.

In embodiments of this aspect of the disclosure, the formulations can further comprise an aqueous carrier, wherein the aqueous carrier optionally comprises a vitamin, a nutraceutical, a coloring agent, a flavoring agent, or a combination thereof.

In embodiments of this aspect of the disclosure, tin he formulations the amount of orthophosphoric acid can be between about 4 ml to about 80 ml, the amount of vegetable oil can be between about 0.25 ml to about 20 ml, and the amount of folic acid can be between about 0.1 mg-10 mg, and water, in a final volume of 100 ml.

In some embodiments, the vegetable oil can be olive oil.

In the embodiments the formulation further comprises water.

In embodiments of this aspect of the disclosure, the formulation can further comprise at least one of the group consisting of magnesium citrate, magnesium aspartate, malic acid, L-carnitine, alpha-ketoglutaric acid, co-enzyme Q10, glycerol, inositol, and choline bitartrate.

Embodiments of this aspect of the disclosure can further comprise magnesium citrate, magnesium aspartate, malic acid, L-carnitine, alpha-ketoglutaric acid, co-enzyme Q10, glycerol, inositol, and choline bitartrate.

In some embodiments of the formulation of the disclosure, the formulation can comprise, in a final volume of 100 ml: ortho-phosphoric acid between about 4 ml to about 16 ml; vegetable oil between about 0.25 ml to about 10 ml; folic acid between about 0.1 mg-10 mg; malic acid between about 1 mg and about 5000 mg; magnesium citrate between about 1 mg and about 5000 mg; magnesium aspartate between about 1 mg and about 100 mg; L-carnitine between about 1 mg and about 1000 mg; alpha-ketoglutaric acid between about 1 mg and about 1000 mg; choline bitartrate between about 1 mg and about 100 mg; inositol between about 1 mg and about 100 mg; glycerol between about 0.1 ml and about 5 ml; and water. In these embodiments, the formulation can further comprise Q10 between about 0.05 mg and about 1000 mg, and riboflavin, wherein the amount of riboflavin provides a yellow color to the formulation.

In one embodiment of this aspect of the disclosure, the formulation comprises, in a final volume of 100 ml: ortho-phosphoric acid, about 8.5 ml; vegetable oil, about 1.2 ml; folic acid, about 2.1 mg; malic acid, about 85 mg; magnesium citrate, about 170 mg; magnesium aspartate, about 17 mg; L-carnitine, about 85 mg; alpha-ketoglutaric acid, 127 mg; choline bitartrate, about 11 mg; inositol, about 23 mg; glycerol between about 0.1 ml and about 0.5 ml; and water. This embodiment of the disclosure can further comprise Q10 between about 0.05 mg and about 1000 mg, and riboflavin, wherein the amount of riboflavin provides a yellow color to the formulation.

Another aspect of the disclosure encompasses methods for alleviating neuropathy related pain in subject animal or human, comprising: providing to a subject in need of relief from neuropathy related pain an effective dose of a formulation comprising orthophosphoric acid, a vegetable oil comprising an esterified mono-unsaturated fatty acid, folic acid, and water, wherein the amount of orthophosphoric acid is between about 4 ml to about 80 ml, the amount of a vegetable oil comprising an esterified mono-unsaturated fatty acid is between about 0.25 ml to about 20 ml, the amount of folic acid is between about 0.1 mg-10 mg, and the amount of water is about 200 mls.

In embodiments of this aspect of the disclosure, the formulation can further comprise at least one of the group consisting of magnesium citrate, magnesium aspartate, malic acid, L-carnitine, alpha-ketoglutarc acid, co-enzyme Q10, glycerol, inositol, and choline bitartrate, and optionally a coloring agent, a flavoring agent, or a combination thereof.

In one embodiment of this aspect of the disclosure, the formulation can comprise, in a final volume of 100 ml: orthophosphoric acid, about 8.5 ml; a vegetable oil comprising an esterified mono-unsaturated fatty acid, about 1.2 ml; folic acid, about 2.1 mg; malic acid, about 85 mg; magnesium citrate, about 170 mg; magnesium aspartate, about 17 mg; L-carnitine, about 85 mg; alpha-ketoglutaric acid, 127 mg; choline bitartrate, about 11 mg; inositol, about 23 mg; glycerol between about 0.1 ml and about 0.5 ml; and water. In this embodiment of the disclosure, the formulation can further comprise Q10 between about 0.05 mg and about 1000 mg, and riboflavin, wherein the amount of riboflavin provides a yellow color to the formulation.

In the embodiments of the methods of this aspect of the disclosure, the formulation can be provided to the subject sublingually.

In the embodiments of the methods of this aspect of the disclosure, the formulation can be diluted with water and the subject receives the formulation orally.

The specific examples below are to be construed as merely illustrative, and not limitative of the remainder of the disclosure in any way whatsoever. Without further elaboration, it is believed that one skilled in the art can, based on the description herein, utilize the present disclosure to its fullest extent. All publications recited herein are hereby incorporated by reference in their entirety.

It should be emphasized that the embodiments of the present disclosure, particularly, any "preferred" embodiments, are merely possible examples of the implementations, merely set forth for a clear understanding of the principles of the disclosure. Many variations and modifications may be made to the above-described embodiment(s) of the disclosure without departing substantially from the spirit and principles of the disclosure. All such modifications and variations are intended to be included herein within the scope of this disclosure, and the present disclosure and protected by the following claims.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is at or near atmospheric. Standard temperature and pressure are defined as 20° C. and 1 atmosphere.

EXAMPLES

Example 1

A formulation: orthophosphoric acid, 4-80 ml; olive oil, 0.25 ml-20 ml; folic acid, 0.1 mg-10 mg.

Example 2

In preparing any of the formulations of this and any of the following examples, the order in which the components are combined may be varied. However a preferred order comprises adding dry components to the orthophosphoric acid followed by vigorous agitation. The mono-unsaturated fatty acid component may then be added with further agitation to form a an emulsion or near-emulsion. The water component may then be added with a final mixing to provide a homogeneous or near homogenous liquid. It is contemplated, however, that the mixing order may tolerate some variation such as adding the dry components to the water before adding to the orthophosphoric acid and the mono-saturated fatty acid.

A formulation: orthophosphoric acid, 4-80 ml; olive oil, 0.25 ml-20 ml; folic acid, 0.1 mg-10 mg; and water 200 ml.

Example 3

A formulation: orthophosphoric acid, 4-80 ml; olive oil, 0.25 ml-20 ml; folic acid, 0.1 mg-10 mg; magnesium citrate, 0.1 g-10 g; magnesium aspartate, 0.1 g-10 g; malic acid, 5 mg-5 g; L-carnitine, 5 mg-5 g; alpha-ketoglutaric acid, 0.1 g-5 g; co-enzyme Q10, 1 mg-5 g; glycerol, 1 drop-1500 drops; inositol, 1 mg-3 g; and choline bitartrate, 1 mg-3 g; riboflavin sufficient to impart a deep yellow color, and water 200 ml. Other than the orthophosphoric acid, olive oil and folic acid, and water, the other constituents are optional depending on the needs and degree and complexity of the symptoms experienced by the subject.

Example 4

A formulation for administering to a subject in need of relief from the symptoms of fibromyalgia: orthophosphoric acid, 4-80 ml; olive oil, 0.25 ml-20 ml; folic acid, 0.1 mg-10 mg; magnesium citrate, 0.1 g-10 g; magnesium aspartate, 0.1 g 10 g; malic acid, 5 mg-5 g; L-carnitine, 5 mg-5 g; alpha-ketoglutaric acid, 0.1 g-5 g; co-enzyme Q10, 1 mg-5 g; glycerol, 1 drop-1500 drops; inositol, 1 mg-3 g; and choline bitartrate, 1 mg-3 g; riboflavin sufficient to impart a deep yellow color, and water 200 ml. The basic formulation is then diluted with water in the ratio of 9-12 ml of the formulation to 1-5-3.0 fluid ounces of water. Alternative doses include 6-9 ml of the basic formulation to 1.5-3 fluid ounces of water.

Example 5

|  | Amount per 236 ml final volume (8 U.S. Fluid Ounces) | Amount per 100 ml final volume |
|---|---|---|
| Ortho-phosphoric acid | 20 ml | 8.48 ml |
| Mono-unsaturated fatty acid | 3 ml | 1.28 ml |
| Folic acid | 5 mg | 2.1 mg |
| Malic acid | 200 mg | 84.75 mg |
| Magnesium citrate | 400 mg | 169.5 mg |
| Magnesium aspartate | 40 mg | 16.95 mg |
| L-carnitine | 200 mg | 84.75 mg |
| alpha-ketoglutaric acid | 300 mg | 127.1 mg |
| Choline bitartrate | 25.92 mg | 10.98 mg |
| Inositol | 54.72 mg | 23.19 mg |
| Glycerol | 0.2-0.7 ml | 0.085-0.3 ml |
| Water | to 236 ml |  |
| Q10 | 0.1-200 mg | 0.04-8 mg |
| Riboflavin | to color | to color |

Example 6

The administered dose is dependent on the severity of the perceived pain of the subject. An initial dose of between 9 ml and 12 ml of the stock solution, shown in Table 1) is diluted in between about 1.5 fluid ounces and 3.0 fluid ounces of water. The subject receives the full diluted dose and is retested for pain severity within about 30 secs. If there is no evident relief of pain experienced, a second dose of the formulation may be given. The second dose is between 6 ml and 9 ml of the stock solution diluted by the same amount of water as before, and again fully ingested by the subject. The subject is repalpated after about 30 secs. On rare occasions, pain symptoms still show no sign of diminishing, and a third dose may be required. The full effects of symptom relief may be seen within 15 minutes of administering the first dose.

I claim:

1. A formulation for the relief of neuropathy pain associated with fibromyalgia consisting of orthophosphoric acid, a vegetable oil comprising an esterified mono-unsaturated fatty acid, folic acid, magnesium citrate, magnesium aspartate, malic acid, L-carnitine, alpha-ketoglutaric acid, co-enzyme Q10, glycerol, inositol, choline bitartrate, water, and optionally riboflavin.

2. The formulation of claim 1, consisting of, in a final volume of 100 mL: orthophosphoric acid between about 4 mL to about 16 mL; vegetable oil between about 0.25 mL to about 10 mL; folic acid between about 0.1 mg to about 10 mg; malic acid between about 1 mg and about 5000 mg; magnesium citrate between about 1 mg and about 5000 mg; magnesium aspartate between about 1 mg and about 100 mg; L-carnitine between about 1 mg to about 1000 mg; alpha-ketoglutaric acid between about 1 mg and about 1000 mg; choline bitartrate between about 1 mg and about 100 mg; inositol between about 1 mg and about 100 mg; glycerol between about 0.1 mL and about 5 mL; Q10 between about 0.05 mg and about 1000 mg; and water, and optionally riboflavin.

3. A formulation consisting of, in a final volume of 100 mL: ortho-phosphoric acid, about 8.5 mL; vegetable oil, about 1.2 mL; folic acid, about 2.1 mg; malic acid, about 85 mg; magnesium citrate, about 170 mg; magnesium aspartate, about 17 mg; L-carnitine, about 85 mg; alpha-ketoglutaric acid, about 127 mg; choline bitartrate, about 11 mg; inositol, about 23 mg; glycerol between about 0.1 mL and about 5 mL; Q10 between about 0.05 mg and about 1000 mg, water, and optionally riboflavin.

4. A method for alleviating neuropathy related pain in subject animal or human, comprising:
providing to a subject in need of relief from neuropathy related pain an effective dose of a formulation consisting of orthophosphoric acid,
a vegetable oil comprising an esterified mono-unsaturated fatty add, folic acid, magnesium citrate, magnesium aspartate, malic acid, L-carnitine, alpha-ketoglutaric acid, co-enzyme Q10, glycerol, inositol, choline bitartrate, water, and optionally riboflavin.

5. The method of claim 4, wherein the formulation consists of, in a final volume of 100 mL: ortho-phosphoric acid, about 8.5 mL; a vegetable oil, about 1.2 mL; folic acid, about 2.1 mg; malic acid, about 85 mg; magnesium citrate, about 170 mg; magnesium aspartate, about 17 mg; L-carnitine, about 85 mg; alpha-ketoglutaric acid, about 127 mg; choline bitartrate, about 11 mg; inositol, about 23 mg; glycerol between about 0.1 mL and about 0.5 mL; Q10 between about 0.05 mg and about 1000 mg, water, and optionally riboflavin.

6. The method of claim 4, wherein the formulation is provided to the subject sublingually.

* * * * *